US00PP27106P3

(12) United States Plant Patent
Zaiger et al.

(10) Patent No.: US PP27,106 P3
(45) Date of Patent: Aug. 30, 2016

(54) INTERSPECIFIC TREE NAMED 'PISMO'

(50) Latin Name: ***Interspecific Prunus* species**
Varietal Denomination: PISMO

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 94 days.

(21) Appl. No.: 14/544,290

(22) Filed: Dec. 22, 2014

(65) Prior Publication Data

US 2016/0183422 P1 Jun. 23, 2016

(51) Int. Cl.
*A01H 5/08* (2006.01)

(52) U.S. Cl.
USPC ..... Plt./180

(58) Field of Classification Search
USPC ..... Plt./180
See application file for complete search history.

*Primary Examiner* — Susan McCormick Ewoldt

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree with a vigorous, semi-spreading growth habit.
2. Tree with heavy and regular production of medium to large size fruit.
3. Fruit with an attractive orange-red skin color.
4. Fruit with good flavor and eating quality and an average Brix of 18.7°.
5. Fruit with good handling and shipping quality.

1 Drawing Sheet

Botanical designation: Interspecific *Prunus* species.
Variety denomination: 'PISMO'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

PRIOR VARIETIES

Among the existing varieties of plum, apricot and interspecific trees, which are known to us, and mentioned herein, 'Coral-Cot' Interspecific (U.S. Plant Pat. No. 19,563), our proprietary non-patented apricot seedling selection '311LN217' and our proprietary non-patented interspecific seedling selections '11ME474' and '39ZD1053'.

STATEMENT REGARDING FEDERALLY SPONSORED RESEARCH AND DEVELOPMENT

Not applicable.

ORIGIN OF THE VARIETY

The new variety of interspecific tree, a combination of crosses between *Prunus armeniaca* and *Prunus salicina* was originated by us in our experimental orchard located near Modesto, Calif. from an open pollinated, non-patented interspecific seedling selection with the field identification number '11ME474'. The seed parent (11ME474) originated as a first generation seedling from a cross between our proprietary non-patented apricot seedling '311LN217' and our proprietary non-patented interspecific seedling '39ZD1053'. A large number of these open pollinated seedlings were budded onto established trees of 'Nemaguard' Rootstock (non-patented) to enhance earlier fruit production. Under close and careful observation the present seedling exhibited desirable fruit and tree characteristics and was selected in 2011 for additional asexual propagation and commercialization.

ASEXUAL REPRODUCTION OF THE VARIETY

In 2011 asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new and distinct variety of interspecific tree Apricot×[(Plum×Plumcot)×(Apricot×PlumCot)×(Plum×PlumCot)] is of large size, semi-spreading growth and a regular and productive bearer of medium to large size, orange flesh, freestone fruit with good flavor and eating quality. The fruit is further characterized by having an attractive orange/red skin color and having good storage and shipping quality. In comparison to its non-patented interspecific seed parent (11ME474) the fruit of the new variety has orange flesh compared to yellow and is approximately 14 days earlier in maturity. In comparison to the commercial variety 'Coral-Cot' Interspecific (U.S. Plant Pat. No. 19,563) the fruit of the new variety has a more attractive orange/red skin color and has improved flavor.

DESCRIPTION OF THE PHOTOGRAPH

The accompanying color photographic illustration shows typical specimens of the foliage and fruit of the present new interspecific variety.

The illustration shows the upper and lower surface of the leaves, an exterior and sectional view of a single fruit divided in its suture plane to show flesh color, pit cavity and the stone remaining in place.

The photographic illustration was taken shortly after being picked (shipping ripe) from a 5 year old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 5 year old specimens grown near Modesto, Calif., with color in accordance with Munsell Book of Color published in 1958.

Tree:

*Size.*—Large, usually pruned to 3 to 3.5 meters in height and width for economical harvesting of fruit. Varies with different cultural practices.

*Vigor.*—Vigorous, growth of 1.5 to 2 meters in height the first growing season. Varies with soil type, fertility of soil and climatic conditions.

*Form.*—Semi-spreading, usually pruned to vase shape.

*Branching habit.*—Semi-spreading, crotch angle approximately 35°, increases with heavy crop load.

*Productivity.*—Productive, thinning and spacing of fruit necessary for desired market size. Fruit set varies with climatic conditions during bloom time.

*Bearer.*—Regular, adequate fruit set 3 consecutive years. No alternate bearing observed.

*Fertility.*—Partially self-fertile, pollinator recommended.

*Density.*—Medium dense, usually pruned to vase shape to allow more sunlight to center of tree to enhance fruit color and health of fruit spurs.

*Hardiness.*—Tree grown in USDA Hardiness Zone 9. Winter chilling requirement approximately 700 hours at or below 45° F. Hardy in all stone fruit growing areas of California.

Trunk:

*Size.*—Medium to large. Average circumference 62.5 cm at 10.2 cm above ground on a 5 year old tree.

*Stocky.*—Medium stocky.

*Texture.*—Medium shaggy, roughness increases with age of growth.

*Color.*—Varies from 5Y 3/2 to 7.5Y 4/2.

Branches:

*Size.*—Medium. Average circumference 19.9 cm at 1.2 meters above ground. Crotch angle approximately 35°, increases with heavy crop load.

*Surface texture.*—New growth relatively smooth. Mature growth medium rough, roughness increases with age.

*Lenticels.*—Average number 37 in a 25.8 sq cm surface area of branch. Average length 3.1 mm. Average width 1.9 mm. Color varies from 7.5YR 6/8 to 7.5YR 5/8.

*Color.*—New growth varies from 7.5R 2/6 to 2.5GY 5/6. Old growth varies from 7.5YR 6/8 to 7.5YR 4/2, varies with age of growth.

Leaves:

*Size.*—Medium. Average length 74.0 mm. Average width 60.7 mm.

*Form.*—Ovate.

*Apex.*—Acuminate.

*Base.*—Cuneate.

*Margin.*—Doubly serrate.

*Thickness.*—Medium.

*Surface texture.*—Upper surface relatively smooth, slight indentations over midrib and leaf veins. Lower surface relatively smooth, except for small ridges created by midrib and pinnate venation. Both upper and lower surfaces glabrous.

*Petiole.*—Medium. Average length 28.8 mm. Average width 1.2 mm. Longitudinally grooved. Surface — glabrous. Color varies from 7.5Y 7/4 to 5R 3/8.

*Glands.*—Size — small to medium. Type — globose. Average length 0.9 mm. Average diameter 0.7 mm. Average number 3, varies from 2 to 4. Located primarily on the upper portion of the petiole and base of leaf blade. Color varies from 5R 3/6 to 5R 3/4.

*Stipules.*—Average length 6.0 mm. Average number 2. Edges — pectinate. Color varies from 5R 3/6 to 2.5GY 6/8.

*Color.*—Upper surface varies from 5GY 5/6 to 5GY 4/6. Lower surface varies from 5GY 5/4 to 5GY 6/4. Midvein color varies from 10Y 6/4 to 10Y 7/4.

Flower buds:

*Size.*—Large. Average length 14.3 mm. Average diameter 9.1 mm.

*Hardiness.*—Hardy with respect to California winters.

*Form.*—Conical, becoming slightly elongated just before opening.

*Pedicel.*—Average length 2.5 mm. Average width 1.9 mm. Color varies from 10Y 7/6 to 2.5GY 7/8. Surface — glabrous.

*Density.*—Medium.

*Color.*—Varies from 5RP 6/12 to 5RP 8/6.

*Number of buds per spur.*—Average 12, varies from 7 to 15. Varies with age of spur.

Flowers:

*Blooming period.*—Date of First Bloom Feb. 13, 2014. Date of Petal Fall Feb. 23, 2014, varies slightly with climatic conditions.

*Size.*—Large. Average height 18.8 mm. Average diameter 31.8 mm.

*Petals.*—Number — normally 5, alternately arranged to sepals. Size — large. Average length 15.2 mm. Average width 17.8 mm. Shape — obovate. Arrangement — overlapping. Petal apex — rounded. Petal base — rounded to somewhat truncated. Margin — sinuate. Color varies from 5RP 5/10 to 5RP 8/4, fades with age of flower. Both upper and lower surfaces glabrous.

*Sepals.*—Number — normally 5, alternately arranged to petals. Size — large. Average length 6.0 mm. Average width 6.0 mm. Shape — ovate. Margin — entire.

Apex rounded to triangular. Both upper and lower surfaces glabrous. Color — upper surface varies from 2.5R 3/8 to 2.5R 4/10. Lower surface varies from 2.5R 3/8 to 2.5GY 6/8.

*Stamens.*—Average number per flower 34. Average filament length 13.2 mm. On average, the stamens are even with the height of the petals. Filament color N 9.5/(white). Anther color varies from 5Y 8/10 to 5Y 8.5/10.

*Pollen.*—Partially self-fertile, pollinator recommended. Color varies from 5Y 8/10 to 5Y 8/8.

*Pistil.*—Normally one. Surface — pubescent. Average length 16.3 mm. Position of stigma an average of 1.7 mm below anthers. Color varies from 10Y 7/6 to 2.5GY 7/8.

*Fragrance.*—Slight.

*Color.*—Varies from 2.5RP 9/2 to 5RP 8/4, depending on age of flower.

*Pedicel.*—Average length 2.3 mm. Average width 1.7 mm. Color varies from 10Y 7/6 to 2.5GY 7/8. Surface — glabrous.

*Number flowers per flower bud.*—Average 2, varies from 2 to 3.

Fruit:

*Maturity when described.*—Firm ripe and ready for consumption.

*Date of first picking.*—Jun. 7, 2014.

*Date of last picking.*—Jun. 17, 2014, varies slightly with climatic conditions.

*Size.*—Medium. Average diameter axially 55.2 mm. Average transversely in suture plane 59.8 mm. Average across suture plane 51.1 mm. Average weight 99.4 grams, varies slightly with fertility of the soil, amount of thinning and climatic conditions.

*Form.*—Globose to slightly elongated.

*Suture.*—Lipped, extends from base to apex.

*Ventral surface.*—Lipped.

*Apex.*—Slightly retuse.

*Base.*—Flat.

*Stem cavity.*—Rounded to slightly elongated in suture plane. Average depth 5.0 mm. Average diameter 5.6 mm.

Stem:

*Size.*—Small to medium. Average length 7.5 mm. Average diameter 3.8 mm.

*Color.*—Varies from 5GY 4/8 to 7.5GY 5/6.

Flesh:

*Ripens.*—Evenly.

*Texture.*—Firm, meaty.

*Fibers.*—Few, small, tender.

*Firmness.*—Firm, comparable to commercial apricot varieties.

*Aroma.*—Slight.

*Amydgalin.*—Undetected.

*Eating quality.*—Good.

*Flavor.*—Good.

*Juice.*—Moderate amount, enhances flavor.

*Acidity.*—Not available.

*Brix.*—Average Brix 18.7°, varies slightly with amount of fruit per tree and climatic conditions.

*Color.*—Varies from 5YR 7/10 to 5YR 6/10.

*Pit cavity.*—Average length 32.7 mm. Average width 26.0 mm. Average depth 8.7 mm. Color varies from 2.5YR 6/10 to 2.5YR 6/12.

Skin:

*Thickness.*—Medium.

*Surface.*—Smooth to very slightly waffled.

*Pubescence.*—Moderate amount, short in length.

*Tendency to crack.*—None.

*Color.*—Ground color varies from 5YR 7/12 to 5YR 6/14. Partially overspread with 5R 5/10 to 5R 4/12.

*Tenacity.*—Tenacious to flesh.

*Astringency.*—Undetected.

Stone:

*Type.*—Freestone, weak adherence to flesh.

*Size.*—Large. Average length 29.5 mm. Average width 24.0 mm. Average thickness 13.4 mm.

*Form.*—Ovoid.

*Base.*—Flat.

*Apex.*—Rounded.

*Surface.*—Lightly pitted throughout.

*Sides.*—Unequal, one side extending further outward from suture plane.

*Ridges.*—Very small and short, extending from base towards apex.

*Tendency to split.*—None.

*Color.*—Varies from 10YR 3/4 to 10YR 4/4 when dry.

Kernel:

*Size.*—Large. Average length 21.5 mm. Average width 16.4 mm. Average depth 7.8 mm.

*Form.*—Ovoid.

*Viability.*—Viable, complete embryo development.

*Skin color.*—Varies from 2.5Y 9/4 to 5Y 9/2.

Use: Dessert.

*Market.*—Local and long distance.

Keeping quality: Good, held firm in cold storage for 3 weeks at 38° to 42° F. without shriveling, internal breakdown of flesh or appreciable loss of eating quality.

Shipping quality: Good, showed minimal skin scarring or flesh bruising during picking, packing and shipping trials.

Plant/fruit disease resistance/susceptibility: No specific testing for relative plant/fruit disease resistance/susceptibility has been designed. Under close observation during planting, growing and harvesting of fruit, under normal cultural and growing conditions near Modesto, Calif., no particular plant/fruit disease resistance or susceptibility has been observed. Any variety observed during indexing of plant characteristics with abnormal fungus, bacterial, virus or insect susceptibility is destroyed and eliminated from our breeding program. No atypical resistances/susceptibilities have been noted under normal cultural practices.

The present new variety of interspecific tree, its flowers foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of interspecific tree, substantially as illustrated and described.

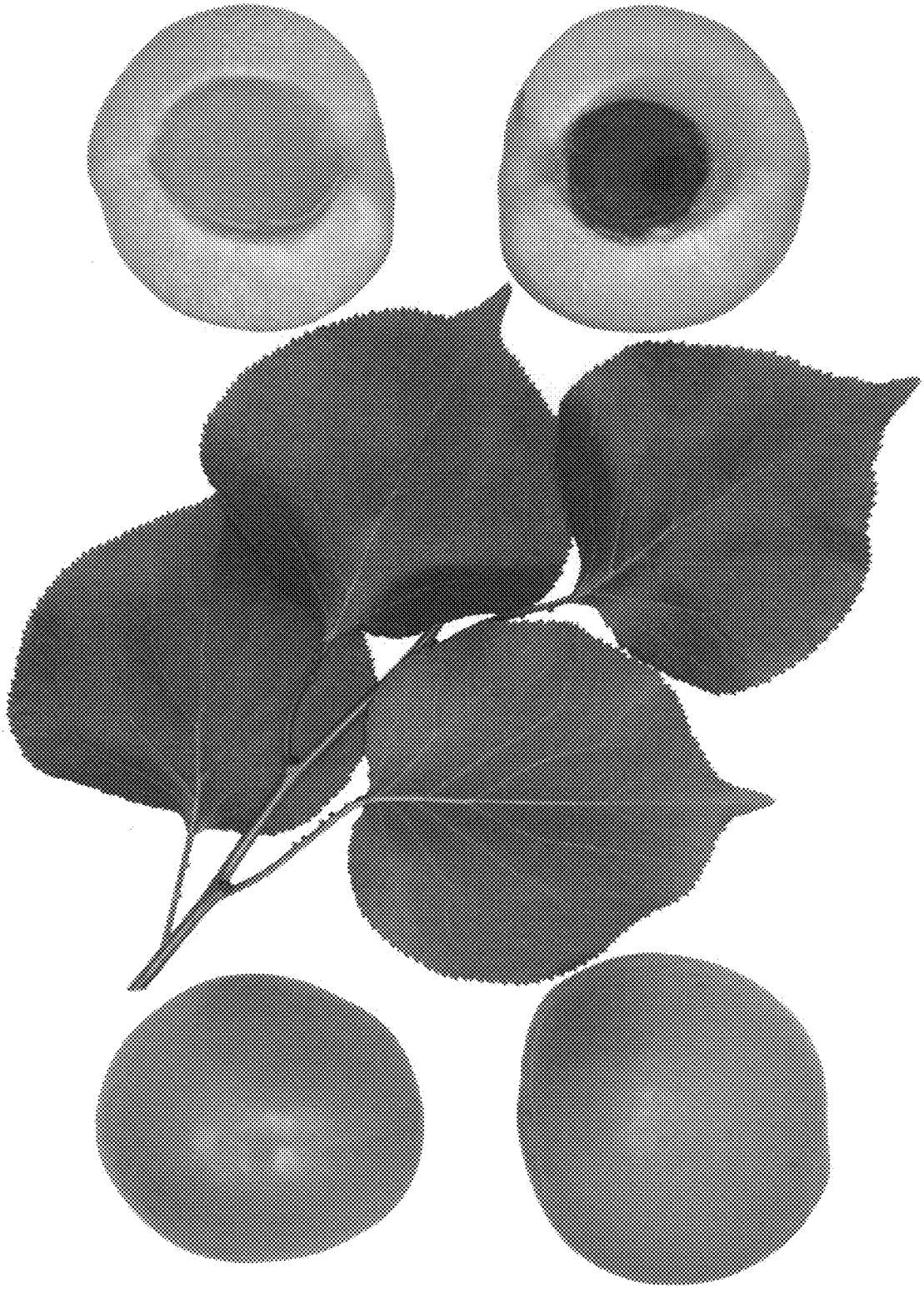

* * * * *